US009072683B2

(12) United States Patent
Cao et al.

(10) Patent No.: US 9,072,683 B2
(45) Date of Patent: *Jul. 7, 2015

(54) USE OF XANTHAN GUM AS A HAIR FIXATIVE

(75) Inventors: Hongjie Cao, Hillsborough, NJ (US); Gary T. Martino, Monmouth Junction, NJ (US); Paul H. Richardson, Vernon, NJ (US)

(73) Assignee: AKZO NOBEL N.V., Arnhem (NL)

( * ) Notice: Subject to any disclaimer, the term of this patent is extended or adjusted under 35 U.S.C. 154(b) by 646 days.

This patent is subject to a terminal disclaimer.

(21) Appl. No.: 10/198,469

(22) Filed: Jul. 18, 2002

(65) Prior Publication Data

US 2003/0143179 A1 Jul. 31, 2003

Related U.S. Application Data

(63) Continuation-in-part of application No. 09/932,435, filed on Aug. 17, 2001.

(51) Int. Cl.
*A61Q 5/00* (2006.01)
*A61K 8/73* (2006.01)
*A61Q 5/06* (2006.01)

(52) U.S. Cl.
CPC .... *A61K 8/73* (2013.01); *A61Q 5/06* (2013.01)

(58) Field of Classification Search
CPC ........... A61K 8/73; A61Q 19/00; A61Q 5/12; A61Q 5/002; A61Q 5/04; A61Q 5/004; A61Q 5/02
USPC ................. 424/401, 70.1, 70.2, 70.11, 78.02, 424/78.03; 514/880, 947
See application file for complete search history.

(56) References Cited

U.S. PATENT DOCUMENTS

| | | | |
|---|---|---|---|
| 3,349,077 A | | 10/1967 | Schweiger |
| 4,465,702 A | | 8/1984 | Eastman et al. |
| 4,477,480 A | | 10/1984 | Seidel et al. |
| 4,591,610 A | | 5/1986 | Grollier |
| 4,595,586 A | | 6/1986 | Flom |
| 5,037,929 A | | 8/1991 | Rajagopalan et al. |
| 5,131,953 A | | 7/1992 | Kasica et al. |
| 5,149,799 A | | 9/1992 | Rubens |
| 5,187,272 A | | 2/1993 | Katcher et al. |
| 5,198,469 A | | 3/1993 | Sakata |
| 5,206,009 A | * | 4/1993 | Watling et al. .......... 424/45 |
| 5,593,503 A | | 1/1997 | Shi et al. |
| 5,679,556 A | | 10/1997 | Homma et al. |
| 5,879,669 A | * | 3/1999 | Clausen et al. ......... 424/70.11 |
| 6,017,860 A | * | 1/2000 | Sajic et al. ............. 510/124 |
| 6,113,881 A | | 9/2000 | Bhatt et al. |
| 6,147,038 A | * | 11/2000 | Halloran ................ 510/122 |
| 6,531,118 B1 | | 3/2003 | Gonzalez et al. |
| 6,716,418 B2 | | 4/2004 | Sen Gupta et al. |
| 6,887,400 B1 | | 5/2005 | Wei et al. |
| 7,014,842 B2 | | 3/2006 | Dueva-Koganov et al. |
| 2003/0049290 A1 | | 3/2003 | Jha et al. |
| 2003/0108505 A1 | | 6/2003 | Cao et al. |
| 2003/0143179 A1 | | 7/2003 | Cao et al. |
| 2003/0228267 A1 | | 12/2003 | Aust et al. |
| 2004/0234486 A1 | | 11/2004 | Hashimoto |

FOREIGN PATENT DOCUMENTS

| | | |
|---|---|---|
| EP | 0 321 216 | 6/1989 |
| EP | 0 554 818 A2 | 8/1993 |
| EP | 0 664 113 | 7/1995 |
| EP | 0 784 970 | 7/1997 |
| EP | 0 823 252 | 2/1998 |
| EP | 0 911 345 A2 | 4/1999 |
| EP | 0784970 * | 5/1999 |
| EP | 1 166 767 | 1/2002 |
| GB | 2 331 302 | 5/1999 |
| GB | 2 380 938 A | 4/2003 |
| JP | 62-263111 | 11/1987 |
| JP | 63-150215 | 6/1988 |
| JP | 05-221838 | 8/1993 |
| JP | 07-061910 | 3/1995 |
| JP | 07-069838 | 3/1995 |
| JP | 07-233034 | 9/1995 |
| JP | 08-231354 | 9/1996 |
| JP | 09-255534 | 9/1997 |
| JP | 10/33125 * | 2/1998 |
| JP | 10067630 | 3/1998 |
| JP | 11-236310 * | 8/1999 |
| JP | 2000-053552 | 2/2000 |
| JP | 2004339108 A | 12/2004 |
| WO | WO 95/04082 | 2/1995 |
| WO | WO 98/09608 | 3/1998 |

(Continued)

OTHER PUBLICATIONS

Derwent Abstract No. 0007832191 of Japanese Patent No. 08-231354.

Derwent Abstract No. 0007114991 of Japanese Patent No. 07-069838.

Derwent Abstract No. 0006501880 of Japanese Patent No. 05-221838.

Derwent Abstract No. 0008415177 of Japanese Patent No. 09-255534.

(Continued)

*Primary Examiner* — Lakshmi Channavajjala

(74) *Attorney, Agent, or Firm* — Norris McLaughlin & Marcus, P.A.

(57) ABSTRACT

The present invention is directed to the use of xanthan gum, particularly heat treated xanthan gum, as a fixative in hair cosmetic compositions. Xanthan gum is advantageous in that it may be used with other hair fixatives and provides rheology modifying and other properties including excellent stiffness, gloss, dry comb, wet comb, non-flake, anti-static, feel and high humidity curl retention.

24 Claims, 1 Drawing Sheet

(56) References Cited

FOREIGN PATENT DOCUMENTS

| | | |
|---|---|---|
| WO | WO 99/15135 | 4/1999 |
| WO | WO 01/96461 A1 | 12/2001 |

OTHER PUBLICATIONS

Derwent Abstract No. 0004242616 of Japanese Patent No. 62-263111.

Derwent Abstract No. 0010037278 of Japanese Patent No. 2000-053552.

Modified Starches: Properties and Uses, Wurzburg, Ed., CRC Press, Inc., Florida (1986).

Starch: Chemistry & Technology, vol. II—Industrial Aspects, Chpt. XXII, "Production & Use of Pregelatinized Starch," R.L. Whistler et al., Ed., pp. 523-536 (1967).

Torres et al, Bioprocess Engineering 12 (1995) 41-46.

National Starch Personal Care Sunscreen Formulation, "Facial Clear Sunscreen Gel SPF 30-Water Resistant 11716-6-7", published Mar. 31, 2004, www.personalcarepolymers.com.

Chinese Office Action for corresponding Chinese Application No. 2008-019104 dated Apr. 30, 2013.

* cited by examiner

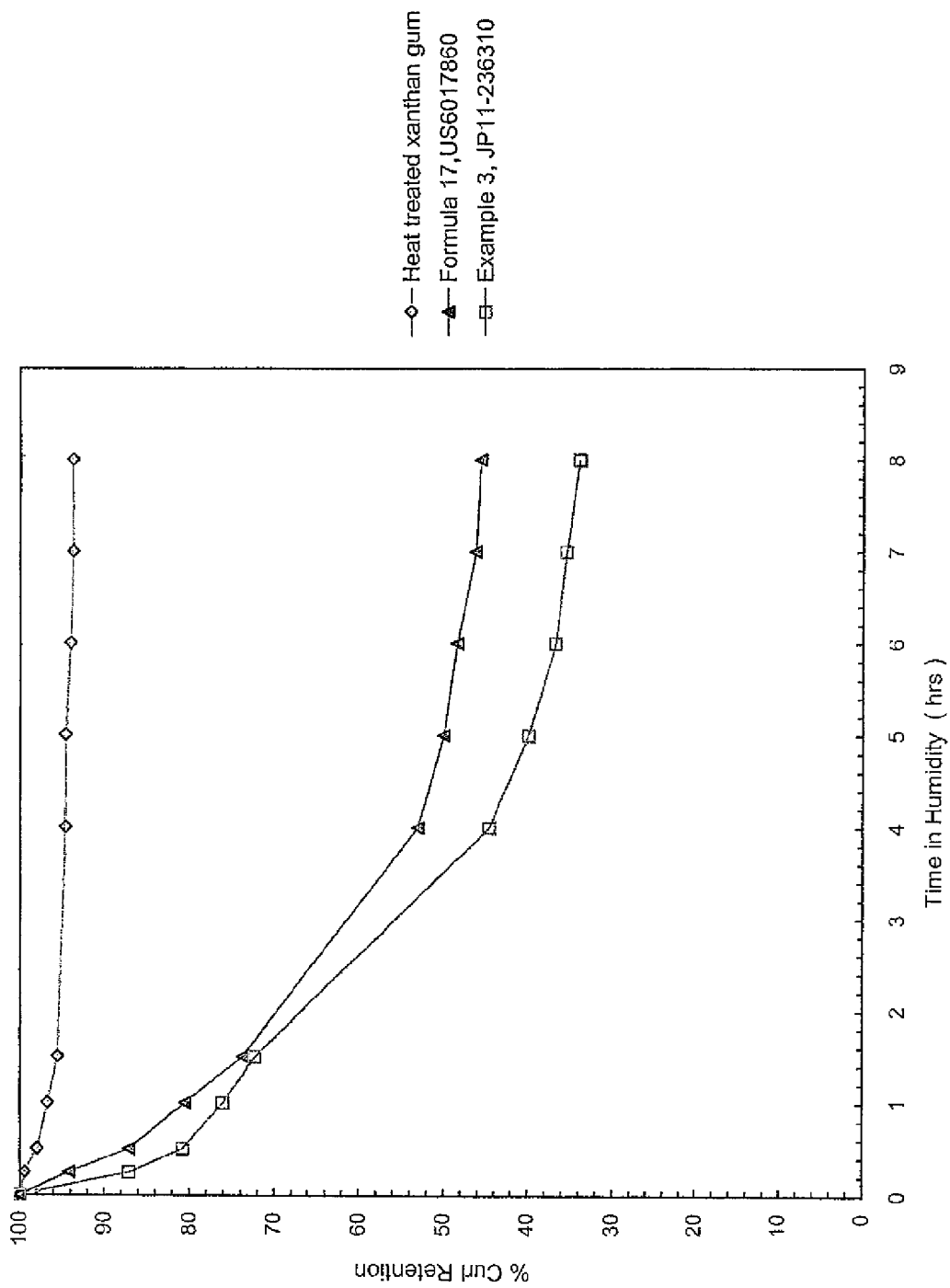

USE OF XANTHAN GUM AS A HAIR FIXATIVE

This application is a continuation-in-part of Ser. No. 09/932,435 filed on Aug. 17, 2001.

BACKGROUND OF THE INVENTION

The present invention relates to the use of xanthan gum, particularly heat treated xanthan gum, as a fixative in hair cosmetic compositions and hair fixative compositions comprising xanthan gum.

Xanthan gum is a polysaccharide gum derived from the bacterium Xanthomonas and is well known in the art. It is composed of a main chain comprising $\beta$-(1,4) D-glucose units. Trisaccharide side chains on alternating anhydroglucose units are composed of a glucuronic acid residue between two mannose units. At most of the terminal mannose units is a pyruvate moiety and the non-terminal mannose carries an acetyl group. It has pseudoplastic or shear-thinning behavior characterized by a decrease in apparent viscosity in response to an increase in shear rate.

Xanthan gum is typically used in many industrial applications as a rheology modifier; thickening, viscosifying and gelling when combined with other polymers. It has also been used to impart stability to emulsions and prevent the settling out of solids. Its limited ability to disperse in either hot or cold water allows xanthan gum to be formulated into a broad variety of applications including pharmaceuticals, household products, foods, and personal care products.

Xanthan gum with an apparent average molecular weight of greater than 16,000,000 has been used to stabilize and improve the feel of emulsified cosmetics such as toilet water, creams and cleansing gels (JP Application No. 10-140503).

Xanthan gum which has been heat-treated is also known in the art. For example, EP 321 216 enhances the viscosity profile of xanthan gum by thermally treating it in the dry state (15% moisture or less). Heat treatment of xanthan gum is also known in JP Application No. 8-193055 which heat treats xanthan gum in the powdered form.

Surprisingly, it has now been discovered that xanthan gum, particularly heat treated xanthan gum, is a suitable fixative for hair cosmetic compositions.

SUMMARY OF THE INVENTION

The present invention is directed to the use of xanthan gum, particularly heat treated xanthan gum, as a fixative in hair cosmetic compositions. Xanthan gum is advantageous in that it may be used with other hair fixatives and provides rheology modifying and other properties including excellent stiffness, gloss, dry comb, wet comb, non-flake, anti-static, feel and high humidity curl retention.

DETAILED DESCRIPTION OF THE INVENTION

The present invention is directed to the use of xanthan gum, particularly heat treated xanthan gum, as a fixative in hair cosmetic compositions.

The xanthan gum may be used in a purified form or may be heat treated. Heat treatment of xanthan gum is typically done at low moisture, particularly less than about 25%, more particularly less than about 8%, most particularly less than about 1%, at a temperature of at least about 60° C., more particularly at least 100° C., and most particularly at least about 105° C. for a period of time of about 30 minutes, particularly at least one hour, more particularly at least 2.5 hours.

The moisture content, pH, temperature and time of heat treatment may be adjusted by one skilled in the art to achieve the viscosity, dispersibility, gel texture, solution clarity, and other properties desired. It will further be dependent upon the starting material used (grade, viscosity, molecular weight, and particle size). Typically, low moisture is used to improve the impact of heat-treatment. However, at any given moisture, increasing the temperature or time generally increases viscosity to a maximum and further heating decreases the viscosity of the xanthan gum at the concentrations used in this invention. Acidic pH are typically more suitable; a pH of 2-4 is most suitable.

Heat treatment of xanthan gum may be accomplished by a variety of methods known in the art including without limitation oven, fluidized bed, infrared and microwave heat treatments. The particle size of the resultant heat-treated xanthan gum may be adjusted using methods known in the art such as milling.

The xanthan gum may further be modified either before or after heat treatment. The xanthan gum may be converted by oxidation, enzyme conversion, acid hydrolysis, heat and/or acid dextrinization, or shear. The xanthan gum may also be chemically, enzymatically or physically modified. Suitable chemical derivatives include esters, such as the acetate, and half esters, such as the succinate, octenyl succinate and tetradecenyl succinate; phosphate derivatives; ethers such as hydroxyalkyl ethers and cationic ethers; or any other derivatives or combinations thereof. Modification may also be by chemical crosslinking. Crosslinking agents suitable for use herein include phosphorus oxychloride, epichlorohydrin, sodium trimetaphosphate and adipic-acetic mixed acid anyhrides. Such processes are also known in the art. Typically, the xanthan gum will not be modified other than by crosslinking or heat treatment.

The xanthan gum may also be purified by any method known in the art to remove off flavors and colors that are native to the xanthan gum or are created during the modification or heat treatment processes as long as the heat treatment is not substantially impacted.

Particularly suitable heat treated xanthan gums are those which, in a 1% aqueous solution, has a viscosity of greater than about 4000 cps, more particularly greater than about 6000 cps, most particularly greater than about 8000 cps and a crossover strain of less than about 100, more particularly less than about 90, most particularly less than about 80. Viscosity is measured using a Brookfield DV-I viscometer with a Spindle #6 at 10 rpm. Crossover strain, as used herein, is measured using a controlled stress or strain rheometer at a frequency of 1 rad/s and 25° C. The tangent of the phase angle, tangent of delta (tandelta) is plotted versus the strain amplitude and the crossover strain is that at which the tandelta is equal to one.

The resultant heat-treated xanthan gum has improved dispersibility, such that under given conditions of temperature and agitation, the time to fully disperse the resultant gum is typically reduced by 25%, more particularly 50%, most particularly 70% compared to non-heat treated xanthan.

Xanthan gum, native or heat treated, provides fixative properties to hair cosmetic compositions including hair sprays, gels including spray gels, styling lotions, creams, pomades, and mousses. The use of xanthan gum imparts not only stiffness, but is also highly suitable for retention of curls under high humidity conditions. High humidity conditions, as used herein, is intended to mean at 22° C. and 90% relative humidity.

Xanthan gum is particularly suitable for gels as it provides clear to translucent clarity and is easy to use as it is dispersible in either hot or cold water and needs no neutralization. Xanthan gum also exhibits tolerance to salt and extreme pH, particularly in the range of about 2 to about 12. Finally, it is biodegradable and may be labeled as natural.

The heat modification of xanthan gum improves the ease of use, including the ease of dispersing in solution with less tendency to form fish eyes. Heat modification also may be used to improve thickening efficiency and gel texture, reducing the stringiness or pituitousness of the long texture. In addition, heat treatment of xanthan increases its viscosity throughout the pH and salt ranges typically used in hair cosmetic compositions. Unlike Carbomer, xanthan gum is compatible with anionic, cationic or nonionic polymers, allowing it to be formulated with a variety of commonly used hair cosmetic additives. Although xanthan gum alone provides fixative properties, it may be used in combination with other fixatives, including without limitation polyoxythylenated vinyl acetate/crotonic acid copolymers, vinyl acetate crotonic acid (90/10) copolymers, vinyl acetate/crotonic acid/vinyl neodecanoate terpolymers, N-octylacrylamide/methylacrylate/hydroxypropyl methacrylate/acrylic acid/tert-butylaminoethyl methacrylate copolymers, and methyl vinyl ether/maleic anhydride (50/50) copolymers monoesterified with butanol or ethanol, acrylic acid/ethyl acrylate/N-tert-butylacrylamide terpolymers, and poly (methacrylic acid/acrylamidomethyl propane sulfonic acid), acrylates copolymer, octylacrylamide/acrylates/butylaminoethyl methacrylate copolymer, acrylates/octylacrylamide copolymer, VA/crotonates/vinyl Neodeanoate copolymer, poly(N-vinyl acetamide), poly(N-vinyl formamide), corn starch modified, sodium polystyrene sulfonate, polyquaterniums such as polyquaternium-4, polyquaternium-7, polyquaternium-10, polyquaternium-11, polyquarternium-16, polyquaternium-28, polyquaternium-29, polyquaternium-46, polyether-1, polyurethanes, VA/acrylates/lauryl methacrylate copolymer, adipic acid/dimethylaminohydroxypropyl diethylene AMP/acrylates copolymer, methacrylol ethyl betaine/acrylates copolymer, PVP/dimethylaminoethylmethacrylate copolymer, PVP/DMAPA acrylates copolymer, PVP/vinylcaprolactam/DMAPA acrylates copolymer, vinyl caprolactam/PVP/dimethylaminoethyl methacrylate copolymer, VA/butyl maleate/isobornyl acrylate copolymer, VA/crotonates copolymer, acrylate/acrylamide copolymer, VA/crotonates/vinyl propionate copolymer, vinylpyrrolidone/vinyl acetate/vinyl propionate terpolymers, VA/crotonates, cationic and amphoteric guar, polyvinylpyrrolidone (PVP), polyvinylpyrrolidone/vinyl acetate copolymer, PVP acrylates copolymer, vinyl acetate/crotonic acid/vinyl proprionate, acrylates/acrylamide, acrylates/octylacrylamide, acrylates/hydroxyacrylates copolymer, and alkyl esters of polyvinylmethylether/maleic anhydride, diglycol/cyclohexanedimethanol/isophthalates/sulfoisophthalates copolymer, vinyl acetate/butyl maleate and isobornyl acrylate copolymer, vinylcaprolactam/PVP/dimethylaminoethyl methacrylate, vinyl acetate/alkylmaleate half ester/N-substituted acrylamide terpolymers, vinyl caprolactam/vinylpyrrolidone/methacryloamidopropyl trimethylammonium chloride terpolymer, methacrylates/acrylates copolymer/amine salt, polyvinylcaprolactam, polyurethanes, hydroxypropyl guar, hydroxypropyl guar hydroxypropyl trimmonium chloride, poly (methacrylic acid/acrylamidomethyl propane sulfonic acid, poylurethane/acrylate copolymers and hydroxypropyl trimmonium chloride guar, particularly acrylates copolymer, octylacrylamide/acrylates/butylaminoethyl methacrylate copolymer, acrylates/octylacrylamide copolymer, VA/crotonates/vinyl Neodeanoate copolymer, poly(N-vinyl acetamide), poly(N-vinyl formamide), polyurethane, corn starch modified, sodium polystyrene sulfonate, polyquaternium-4, polyquarternium-10, and polyurethane/acrylates copolymer.

Optional conventional additives may also be incorporated into the hair compositions of this invention to provide certain modifying properties to the composition. Included among these additives are silicones and silicone derivatives; humectants; moisturizers; plasticizers, such as glycerine, glycol and phthalate esters and ethers; emollients, lubricants and penetrants, such as lanolin compounds; fragrances and perfumes; UV absorbers; dyes, pigments and other colorants; anticorrosion agents; antioxidants; detackifying agents; combing aids and conditioning agents; antistatic agents; neutralizers; glossifiers; preservatives; proteins, protein derivatives and amino acids; vitamins; emulsifiers; surfactants; viscosity modifiers, thickeners and rheology modifiers; gelling agents; opacifiers; stabilizers; sequestering agents; chelating agents; pearling agents; aesthetic enhancers; fatty acids, fatty alcohols and triglycerides; botanical extracts; film formers; and clarifying agents. Such additives are commonly used in hair cosmetic compositions known heretofore. These additives are present in small, effective amounts to accomplish their function, and generally will comprise from about 0.01 to 10% by weight each, and from about 0.01 to 20% by weight total, based on the weight of the composition.

Aesthetic enhancers is intended to include without limitation aluminum starch octenyl succinate, corn starch modified, aluminum starch octenylsuccinate (and) lauroyl lysine, and aluminum starch octenylsuccinate (and) boron nitride. Thickeners and rheology modifiers is intended to include without limitation acrylates/steareth-20 itaconate copolymer, acrylates/ceteth-20 itaconate copolymer, potato starch modified, hydroxypropyl starch phosphate, acrylates/aminoacrylates/C10-30 alkyl PEG-20 itaconate copolymer, carbomer, acrylates/C10-30 alkyl acrylate crosspolymer, hydroxypropylcellulose, hydroxyethylcellulose, sodium carboxymethylcellulose, polyacrylamide (and) C13-14 isoparaffin (and) laureth-7, acrylamides copolymer (and) mineral oil (and) C13-14 isoparaffin (and) polysorbate 85, hydroxyethylacrylate/sodium acrylol dimethyltaurate copolymer, and hydroxyethylacrylate/sodium acrylol dimethyltaurate copolymer.

Xanthan gum may be formulated into hair cosmetic compositions at any level which provides the desired properties. Typically, native xanthan gum will be used in an amount of at least about 0.01%, particularly at least about 0.2%, more particularly at least about 1.0% and less than about 20%, particularly less than about 10%, more particularly less than about about 3%. In contrast, heat treated xanthan gum will be used in an amount of at least about 0.01%, particularly at least about 0.5%, more particularly at least about 0.75% and less than about 20%, particularly less than about 2%, more particularly less than about 1.5%. The amount used will depend not only upon the properties desired, but also upon the heat treatment levels and other additives. For example, the same amount of fixative property may be achieved by using less xanthan gum and adding another commonly used hair fixative polymer.

The hair cosmetic composition may be prepared by dispersing xanthan gum in water and then mixing in the remaining hair cosmetic components such as any fixative polymers, conditioning polymers or other additives as desired.

The delivery system in most cases will be water. However, it is possible to use a solvent. Due to environmental regulations controlling the emission of volatile organic compounds (VOCs) into the atmosphere, VOC emissions in hairsprays have been restricted to 55% in some states, and may soon be restricted to even lower levels. VOC is measured as a wt/wt % based upon the hair cosmetic formulation. As used herein, a volatile organic compound containing from 1 to 10 carbon atoms, which has a vapor pressure of at least 0.1 mm Hg at 20° C., and is photochemically active. Water is generally substituted for at least a portion of the volatile organic compounds and so has become a greater component in hair cosmetic compositions.

In general, the amount of solvent will be small to achieve a VOC content of no more than 55%. For mousses, the amount of solvent will be even smaller to generally achieve a VOC content of no more than 6%. Typically, the solvent will be a lower ($C_{1-4}$) alcohol, particularly methanol, ethanol, propanol, isopropanol, or butanol, though any solvent known in the art may be used.

VOC will also include any optional propellant(s). Such propellants include, without limitation, ethers, such as dimethyl ether; one or more lower boiling hydrocarbons such as $C_3$-$C_6$ straight and branched chain hydrocarbons, for example, propane, butane, and isobutane; halogenated hydrocarbons, such as, hydrofluorocarbons, for example, 1,1-difluoroethane and 1,1,1,2-tetrafluoroethane, present as a liquefied gas; and the compressed gases, for example, nitrogen, air and carbon dioxide.

The hair cosmetic composition may be formulated with xanthan gum to achieve the desired properties. For example the amount of xanthan gum may be adjusted to achieve the desired stiffness and curl retention. In general, a hair gel will have a viscosity of at least about 5,000 cps, more particularly at least about 6,000 cps and most particularly at least about 8,000 cps, a high humidity curl retention for 2 hours of at least about 70%, more particularly at least about 80% and most particularly about 90%, and turbidity of no greater than 100 NTU, particularly no greater than 50 NTU, most particularly no greater than 30 NTU.

EXAMPLES

The following examples are presented to further illustrate and explain the present invention and should not be taken as limiting in any regard. All percents used are on a weight/weight basis.

Example 1

Hair Styling Gels with Native and Heat-treated Xanthan Gum

| Ingredients | Formula 1 % w/w | Formula 2 % w/w |
|---|---|---|
| Part A | | |
| Acrylates Copolymer[1] (50%) | 8.0 | 8.0. |
| Deionized Water | 40.0 | 40.0 |
| Aminomethyl Propanol[2] | 0.56 | 0.56 |
| Part B | | |
| Xanthan gum[3] | 1.0 | — |
| Heat-treated Xanthan gum[4] | — | 1.0 |
| Deionized Water | q.s. | q.s. |
| Preservative | q.s. | q.s. |
| Part C | | |
| Keratin Protein | 0.2 | 0.2 |
| Propylene Glycol | 2.0 | 2.0 |

-continued

| Ingredients | Formula 1 % w/w | Formula 2 % w/w |
|---|---|---|
| Polysorbate 20[5] | 0.5 | 0.5 |
| Fragrance | 0.1 | 0.1 |
| | 100 | 100 |

[1]Balance 0/55 (National Starch and Chemical Co.)
[2]AMP-95 (Angus)
[3]Keltrol T (Kelco)
[4]Heat-treated Keltrol T (Fluid bed reactor at 235° F. for 60 minutes)
[5]Tween 20 (ICI Surfactants)

The ingredients in part A were combined and mixed until clear. In a separate container, xanthan or heat-treated xanthan gum was dispersed into water with moderate mixing (for formula 1, mix for 30 minutes at 700 rpm, and for formula 2, mix for 10 minutes at 700 rpm to achieve uniform part B). Parts A and B were combined while stirring moderately and then part C was added.

Both the xanthan and heat-treated xanthan gum were cold water dispersible. However, the heat-treated xanthan gum was easier to disperse than the native xanthan gum. In addition, no neutralization was needed with the use of xanthan gum.

Formula 1 produced a clear, colorless viscous liquid (Brookfield viscosity: 3200 cps with sprindle#4 @20 rpm). Formula 2 produced a clear, colorless gel (Brookfield viscosity: 8200 cps with sprindle#4 @20 rpm). Formula 2 had much higher viscosity than formula 1, which demonstrated that the heat-treated xanthan gum provides better thickening efficiency. Formula 2 was also much more gel-like, or with shorter and less stringy gel texture compared to formula 1. Both formulas had very good clarity.

Example 2

Various Hair Styling Gel Formulations

| Ingredients | Formula 3 % w/w | Formula 4 % w/w | Formula 5 % w/w | Formula 6 % w/w | Formula 7 % w/w |
|---|---|---|---|---|---|
| Part A | | | | | |
| Acrylates Copolymer[1] (50%) | 8.0 | — | — | — | — |
| Octylacrylamide/ Acrylates/ Butylaminoethyl Methacrylate Copolymer[2] | — | 4.0 | — | — | — |
| Acrylates/ Octylacrylamide Copolymer[3] | — | — | 4.0 | — | — |
| Octylacrylamide/ Acrylates/ Butylaminoethyl Methacrylate Copolymer[4] | — | — | — | 4.0 | — |
| PVP[5] | — | — | — | — | 4.0 |
| Deionized Water | 40.0 | 40.0 | 40.0 | 40.0 | 40.0 |
| Aminomethyl Propanol[6] | 0.56 | 0.94 | 1.13 | 0.77 | — |
| Part B | | | | | |
| Heat-treated Xanthan gum[7] | 0.85 | 0.85 | 0.85 | 0.85 | — |
| Carbomer[8] | — | — | — | — | 0.5 |
| Aminomethyl Propanol | — | — | — | — | 0.29 |

-continued

| Ingredients | Formula 3 % w/w | Formula 4 % w/w | Formula 5 % w/w | Formula 6 % w/w | Formula 7 % w/w |
|---|---|---|---|---|---|
| Deionized Water | q.s. | q.s. | q.s. | q.s. | q.s. |
| Preservative | q.s. | q.s. | q.s. | q.s. | q.s. |
|  | 100 | 100 | 100 | 100 | 100 |

[1]Balance 0/55 (National Starch and Chemical Co.)
[1]Balance 47 (National Starch and Chemical Co.)
[3]Amphomer HC (National Starch and Chemical Co.)
[4]Amphomer (National Starch and Chemical Co.)
[5]PVP K-30 (ISP)
[6]AMP-95 (Angus)
[7]Heat-treated Keltrol T (Fluid bed reactor at 235° F. for 60 minutes)
[8]Carbopol 940 (B F Goodrich)

Formulas 3-6 produced clear to translucent hair gels with viscosity>7000 cps (Brookfield viscosity spindle #4 @20 rpm). As a comparison, formula 7 is a basic formula for the most commonly used commercial hair styling gel. This example shows the compatibility of various anionic fixative polymers with heat-treated xanthan gum.

| Ingredients | Formula 8 % w/w | Formula 9 % w/w | Formula 10 % w/w | Formula 11 % w/w |
|---|---|---|---|---|
| Part A |  |  |  |  |
| Acrylates Copolymer[1] (50%) | 8.0 | — | — | — |
| Octylacrylamide/Acrylates/Butylaminoethyl Methacrylate Copolymer[2] | — | 4.0 | — | — |
| Acrylates/Octylacrylamide Copolymer[3] | — | — | 4.0 | — |
| Octylacrylamide/Acrylates/Butylaminoethyl Methacrylate Copolymer[4] | — | — | — | 4.0 |
| Deionized Water | 40.0 | 40.0 | 40.0 | 40.0 |
| Aminomethyl Propanol[5] | 0.56 | 0.94 | 1.13 | 0.77 |
| Part B |  |  |  |  |
| Carbomer[6] | 0.5 | 0.5 | 0.5 | 0.5 |
| Aminomethyl Propanol | 0.29 | 0.29 | 0.29 | 0.29 |
| Deionized Water | q.s. | q.s. | q.s. | q.s. |
| Preservative | q.s. | q.s. | q.s. | q.s. |
|  | 100 | 100 | 100 | 100 |

[1]Balance 0/55 (National Starch and Chemical Co.)
[2]Balance 47 (National Starch and Chemical Co.)
[3]Amphomer HC (National Starch and Chemical Co.)
[4]Amphomer (National Starch and Chemical Co.)
[5]AMP-95 (Angus)
[6]Carbopol 940 (B F Goodrich)

Formulas 8-11 resulted in cloudy liquid mixtures with low viscosity. This demonstrates the incompatibility of various anionic fixative polymers with Carbomer.

| Ingredients | Formula 12 % w/w | Formula 13 % w/w | Formula 14 % w/w | Formula 15 % w/w |
|---|---|---|---|---|
| Xanthan gum | 2.0 | — | — | — |
| Heat-treated Xanthan gum | — | 1.0 | 2.0 | 0.85 |
| Deionized Water | q.s. | q.s. | q.s. | q.s. |
| Preservative | q.s. | q.s. | q.s. | q.s. |
|  | 100 | 100 | 100 | 100 |

Formulas 12-15 show that hair styling gels can simply contain xanthan gum or heat-treated xanthan gum at desired levels, as well as water and preservatives. Due to the improvement in solution rheology, heat-treated xanthan gum may be used at much lower level than untreated xanthan gum and produce more gel-like product.

| Ingredients | Formula 21 % w/w | Formula 22 % w/w | Formula 23 % w/w |
|---|---|---|---|
| Part A |  |  |  |
| Acrylates Copolymer[1] (50%) | 8.0 | 4.0 | 8.0 |
| Aminomethyl Propanol | 0.56 | 0.28 | 0.56 |
| Deionized Water | 40.0 | 40.0 | 40.0 |
| Part B |  |  |  |
| Heat-treated Xanthan gum[2] | 1.0 | 1.0 | — |
| Xanthan gum[3] | — | — | 1.0 |
| Deionized Water | q.s. | q.s. | q.s |
| Preservative | q.s. | q.s. | q.s |
|  | 100 | 100 | 100 |

[1]Balance 0/55 (National Starch and Chemical Co.)
[2]Heat-treated Keltrol T (Fluid bed reactor at 235° F. for 60 minutes)
[3]Keltrol T (Kelco)

These formulas further show different combinations of xanthan and heat-treated xanthan gum with anionic and non-ionic fixative polymers at different use levels.

| Ingredients | Formula 26 % w/w | Formula 27 % w/w | Formula 28 % w/w | Formula 29 % w/w | Formula 30 % w/w |
|---|---|---|---|---|---|
| Part A |  |  |  |  |  |
| Acrylates Copolymer[1] (50%) | 8.0 | 8.0 | 8.0 | 8.0 | 8.0 |
| Aminomethyl Propanol | 0.56 | 0.56 | 0.56 | 0.56 | 0.56 |
| Deionized Water | 40.0 | 40.0 | 40.0 | 40.0 | 40.0 |
| Part B |  |  |  |  |  |
| Heat-treated Xanthan gum[2] | 1.0 | — | — | — | — |
| Heat-treated Xanthan gum[3] | — | 1.0 | — | — | — |
| Heat-treated Xanthan gum[4] | — | — | 1.0 | — | — |
| Heat-treated Xanthan gum[5] | — | — | — | 1.0 | — |
| Heat-treated Xanthan gum[6] | — | — | — | — | 1.0 |
| Deionized Water | q.s. | q.s. | q.s. | q.s. | q.s. |
| Preservative | q.s. | q.s. | q.s. | q.s. | q.s. |
|  | 100 | 100 | 100 | 100 | 100 |

[1]Balance 0/55 (National Starch and Chemical Co.)
[2]Heat-treated Keltrol T (Fluid bed reactor at 220° F. for 240 minutes)
[3]Heat-treated Keltrol T (Fluid bed reactor at 220° F. for 150 minutes)
[4]Heat-treated Keltrol T (Fluid bed reactor at 228° F. for 90 minutes)
[5]Heat-treated Keltrol T (Fluid bed reactor at 235° F. for 30 minutes)
[6]Heat-treated Keltrol T (oven at 250° F. for 120 minutes)

Formulas 26-30 show hair gels using xanthan gum samples that are heat-treated under different conditions.

| Ingredients | Formula 31 % w/w | Formula 32 % w/w | Formula 33 % w/w | Formula 34 % w/w | Formula 35 % w/w |
|---|---|---|---|---|---|
| Part A | | | | | |
| Poly (N-vinyl acetamide) | 3.0 | 1.0 | — | — | — |
| Poly(N-vinyl formamide) | — | — | 3.0 | — | — |
| Polyurethane | — | — | — | 3.0 | — |
| Corn Starch Modified[1] | — | — | — | — | 1.0 |
| Deionized Water | 40.0 | 40.0 | 40.0 | 40.0 | 40.0 |
| Part B | | | | | |
| Heat-treated Xanthan gum[2] | 1.0 | 1.0 | 1.0 | 1.0 | 1.0 |
| Deionized Water | q.s. | q.s. | q.s. | q.s. | q.s. |
| Preservative | q.s. | q.s. | q.s. | q.s. | q.s. |
| | 100 | 100 | 100 | 100 | 100 |

[1]Amaze (National Starch and Chemical Co.)
[2]Heat-treated Keltrol T (Fluid bed reactor at 235° F. for 60 minutes)

These examples show hair gels made with heat-treated xanthan gum and various fixative polymers at different use levels.

| Ingredients | Formula 36 % w/w | Formula 37 % w/w |
|---|---|---|
| Part A | | |
| Polyquaternium-4[1] | 0.15 | — |
| Polyquaternium-10[2] | — | 0.15 |
| Deionized Water | 40.0 | 40.0 |
| Part B | | |
| Heat-treated Xanthan gum[3] | 1.0 | 1.0 |
| Deionized Water | q.s. | q.s. |
| Preservative | q.s. | q.s. |
| | 100 | 100 |

[1]Celquat H-100 or L-200(National Starch and Chemical Co.)
[1]Celquat SC-230M or Celquat SC-240C (National Starch and Chemical Co.)
[2]Heat-treated Keltrol T (Fluid bed reactor at 235° F. for 60 minutes)

These formulas show that cationic fixative/conditioning polymers can be used at lower levels with heat-treated xanthan gum to produce clear hair gels with good performance and rheology.

| Ingredients | Formula 38 % w/w | Formula 39 % w/w | Formula 40 % w/w | Formula 41 % w/w |
|---|---|---|---|---|
| Part A | | | | |
| Gellan Gum[1] | 0.3 | 0.3 | — | — |
| Carbomer[2] | — | — | 0.1 | 0.3 |
| Deionized Water | 40.0 | 40.0 | 40.0 | 40.0 |
| Aminomethyl Propanol[3] | — | — | q.s. to pH 6 | q.s. to pH 6 |
| Part B | | | | |
| Heat-treated Xanthan gum[4] | 1.0 | — | 1.0 | — |
| Xanthan gum[5] | — | 1.0 | — | 1.0 |
| Deionized Water | q.s. | q.s. | q.s. | q.s. |
| Preservative | q.s. | q.s. | q.s. | q.s. |
| | 100 | 100 | 100 | 100 |

[1]Kelcogel (Kelco)
[2]Carbopol 940 (B F Goodrich)
[3]AMP-95 (Angus)
[4]Heat-treated Keltrol T (Fluid bed reactor at 235° F. for 60 minutes)
[5]Keltrol T (Kelco)

Formulas 38-41 demonstrate that hair gels can be made by combining xanthan or heat-treated xanthan gum with other rheology modifiers/thickeners, such as Gellan gum or carbomer.

Example 3

Hair Styling Gel Performance (I) and Curl Retention

The curl retention properties of the hair styling compositions of the present invention were measured and compared to those of three leading commercial hair styling gel compositions with "ultimate" hair holding power. It is known to one skilled in the art that curl retention correlates directly to hair style retention, or hold, which is one of the most important performance attribute for a hair styling product. The test was conducted at 72° F. (22° C.) and 90% Relative Humidity over a period of 2 hours. The procedure allows for statistical analysis of formulation variables. The percentage curl retention was calculated by: Curl Retention $\% = 100 \times (L - L_t)/(L - L_o)$. where L=length of hair fully extended, $L_o$=initial curl length, $L_t$=curl length at a given time t.

The test was performed on 10" long×2 gram tresses of European virgin brown hair (9 replicate tresses per sample). Cleaned wet hair tresses were combed through to remove tangles and excess water is removed. 0.5 gram of sample hair gel was applied to each tress, gently "worked into" the hair tress and combed through. Curls of hair were made using ½" diameter Teflon mandrel, placed on a tray and dried in an oven overnight. The dried curls were removed from the oven and allowed to cool to room temperature. The curls were suspended from the bound end of the tress on graduated transparent curl retention boards. An initial curl length reading was taken before placing boards and curls into the environment chamber. Then curl lengths were recorded at 15 minutes, 30 minutes, 60 minutes, 90 minutes and 2 hours. Curl retention averages were then calculated. The curl retention results after 2 hours are tabulated in Table 1. The results demonstrate that all the hair styling compositions containing xanthan gum, particularly heat-treated xanthan gum, exhibited dramatically superior curl retention compared to the leading commercial products. This superior curl retention property was achieved with and without other fixative polymers. The type and amount of additional fixative polymers did not vary the curl retention capability significantly with xanthan or heat-treated xanthan gum present. Significantly lower curl retention results were obtained when carbomer is used in the composition instead of xanthan gum, particularly heat-treated xanthan gum.

TABLE 1

| Hair Styling Gel Compositions | Average % Curl Retention Time = 2 hours T = 72° F.; RH = 90% |
|---|---|
| 1% heat-treated xanthan gum (Formula 13) | 91 |
| 2% heat-treated xanthan gum (Formula 12) | 93 |
| 4% Acrylates Copolymer + 1% heat-treated xanthan gum (Formula 21) | 93 |
| 4% Acrylates Copolymer + 1% untreated xanthan gum (Formula 23) | 91 |
| 2% Acrylates Copolymer + 1% heat-treated xanthan gum (Formula 22) | 89 |
| 3% PVP + 1% heat-treated xanthan gum (Formula 18) | 95 |
| 4% PVP + 1% heat-treated xanthan gum (Formula 17) | 84 |
| 4% PVP + | 48 |

TABLE 1-continued

| Hair Styling Gel Compositions | Average % Curl Retention Time = 2 hours T = 72° F.; RH = 90% |
|---|---|
| 0.5% Carbomer (Formula 16) | |
| 3% Poly (N-vinyl acetamide) + 1% heat-treated xanthan gum (Formula 31) | 93 |
| 1% Poly (N-vinyl acetamide) + 1% heat-treated xanthan gum (Formula 32) | 91 |
| Commercial hair gel I (containing PVP, carbomer, and other additives) | 34 |
| Commercial hair gel II (containing PVP/VA copolymer, carbomer, and other additives) | 47 |
| Commercial hair gel III (containing PVP/VA copolymer, PVP, carbomer, and other additives) | 11 |

Example 4

Hair Styling Gel Performance, Stiffness and Other Attributes

Test 1

Subjective evaluation of hair styling compositions containing heat-treated xanthan gum compositions containing PVP and carbomer.

European dark brown hair tresses panelists (10"long, 2 grams weight) with 0.5 grams of the hair styling composition were each rated by eight panelists by giving the samples a score of 1 (worst) to 5 (best) for a variety of properties. The performance attributes tested included stiffness, wet feel, wet comb, dry gloss, dry feel, dry comb, dry flake, and anti-static. Stiffness is used to describe the hardness of hair body, which is also a measure of the amount of hold produced by hair styling compositions. This and similar types of sensory tests are well known by those in the art for the performance assessment of personal care and cosmetic products. A summary of the test results is shown in Table 2.

The overall performance of the hair compositions containing heat-treated xanthan gum was better or comparable to a PVP/carbomer hair gel in stiffness, gloss, dry comb, wet comb, flake, anti-static, and feel. All of the heat-treated xanthan gum containing gels provided better stiffness than the PVP/carbomer gel with the same amount of additional fixative polymers. Formula 1 also provided improved wet feel, wet comb, dry feel, and dry comb comparing to the PVP/carbomer gel.

TABLE 2

Results of Subjective Test 1

Average score based on 1 (worst) to 5 (best) rating scale

| Attribute | Formula 3 | | Formula 4 | | Formula 5 | | Formula 7 control |
|---|---|---|---|---|---|---|---|
| wet feel | 3.8 | S | 2.7 | NS | 2.8 | NS | 2.8 |
| wet comb | 3.8 | S | 2.5 | NS | 2.6 | NS | 2.9 |
| dry gloss | 3.4 | NS | 2.7 | NS | 3.1 | NS | 3.2 |
| Stiffness | 3.8 | S | 3.6 | S | 3.6 | S | 2.3 |
| dry comb | 3.9 | S | 2.8 | NS | 2.7 | NS | 3.2 |
| dry flake | 2.8 | NS | 3.0 | NS | 3.1 | NS | 3.2 |
| anti-static | 1.9 | NS | 2.1 | NS | 2.2 | NS | 2.1 |
| dry feel | 3.4 | S | 2.9 | NS | 2.7 | NS | 2.7 |

S = differences in performance between the sample and the control are regarded as being statistically significant at the 95% confidence level
NS = no differences in performance between the sample and the control are regarded as being statistically significant at the 95% confidence level Test 2

Subjective ranking of six hair styling compositions and three leading commercial hair styling gels was performed on human hair tresses for the performance attributes of stiffness, gloss, and dry flake. This sensory evaluation used a Balanced Incomplete Block Design, with which ranking is based on the intensity of attributes. Nine samples were ranked in groups of two by nine panelists. For each pair of samples, a score of 1 was given for less stiffness, more dry flake, and less gloss, and a score of 2 was given for more stiffness, less dry flake, and more gloss. Based on the design, a total of 36 blocks (or pairs) of samples were prepared. The ranking sum of each attribute for each sample was calculated. Rank sums that differed by more than the least significant difference (LSD=3.5) indicates samples which differed by more than 90% of what we would expect from guessing or random stimuli alone. The hair tress preparation procedure was the same with that used in subjective Test 1. A summary of the test results is shown in Table 3. The higher rank run value indicates better performance on each attribute. The differences in rank sum that were less than LSD (3.5) are considered as no significant difference at 90% confidence level. This ranking test was designed for showing trends or patterns among the samples, but not particularly for the comparison of samples in pairs. Compared to the leading commercial gels, hair compositions containing xanthan gum, particularly heat-treated xanthan gum showed equivalent or better stiffness, gloss, and flake attributes.

TABLE 3

Results of Subjective Test 2

| | Rank Sums (LSD = 3.5) | | |
|---|---|---|---|
| Hair Styling Gel Compositions | Stiffness | Gloss | Flake |
| Commercial hair gel I (containing PVP, carbomer, and other additives) | 12 | 11 | 12 |
| Commercial hair gel II (containing PVP/VA copolymer, carbomer, and other additives) | 11 | 12 | 12 |
| Commercial hair gel III (containing PVP/VA copolymer, PVP, carbomer, and other additives) | 8 | 12 | 9 |
| 4% PVP + 0.5% Carbomer (Formula 16) | 15 | 9 | 10 |
| 4% PVP + 1% heat-treated xanthan gum (Formula 17) | 15 | 13 | 11 |
| 4% Acrylates Copolymer + 1% heat-treated xanthan gum (Formula 21) | 11 | 11 | 15 |
| 1% heat-treated xanthan gum (Formula 13) | 11 | 15 | 13 |
| 2% Acrylates Copolymer + 1% heat-treated xanthan gum (Formula 22) | 12 | 12 | 14 |
| 4% Acrylates Copolymer + 1% untreated xanthan gum (Formula 23) | 13 | 13 | 12 |

Example 5

Measurement of Gel Texture

A Rheometrics DSR SR-200 controlled stress rheometer was used for all measurements. The crossover strain was obtained from an oscillatory shear stress sweep run at a frequency of 1 rad/s, from a stress of 2 to 1000 Pa at 25 C. The tangent of the phase angle, tandelta was plotted versus the strain amplitude and the crossover strain was defined as the strain at which the tand=1. This method was applied only to materials which had values of tandelta<1 at low stresses and which then broke down and had values greater than 1 at high stresses. The crossover strain was typically low for materials with short texture and high for materials with long, cohesive, or stringy textures. The crossover strain data for selected hair gels is in Table 4. The shortness of a leading commercial hair gel containing Carbomer and PVP was also measured as a comparison. Good agreement between the crossover strain data and subjective assessment of the gel texture has been found. As shown in Table 4, the shortness of xanthan gel depended on the degree of heat treatment. The untreated xanthan gum gave more stringy and longer gel texture. The higher treatment temperature and/or longer treatment time tended to give shorter, less stringy gel texture. When appropriate heat treatment conditions were selected, one obtained significantly improved shorter gel texture, which was close to the most commonly used Carbomer gel (a polyacrylic acid thickener).

TABLE 4

| Hair Styling Gel Compositions | Crossover Strain (%) |
|---|---|
| 4% Acrylates Copolymer + 1% untreated xanthan gum (Formula 23) | 155 |
| 4% Acrylates Copolymer + 1% heat-treated xanthan gum (fluid bed @ 220° F. for 120 minutes) | 131 |
| 4% Acrylates Copolymer + 1% heat-treated xanthan gum (fluid bed @ 220° F. for 150 minutes) | 88 |
| 4% Acrylates Copolymer + 1% heat-treated xanthan gum (fluid bed @ 228° F. for 60 minutes) | 150 |
| 4% Acrylates Copolymer + 1% heat-treated xanthan gum (fluid bed @ 228° F. for 90 minutes) | 120 |
| 4% Acrylates Copolymer + 1% heat-treated xanthan gum (fluid bed @ 235° F. for 60 minutes) | 96 |
| 1% heat-treated xanthan gum (fluid bed @ 235° F. for 60 minutes) | 82 |
| Commercial hair gel (containing PVP, carbomer, and other additives) | 73 |

Example 6

Clarity Measurement of Hair Gels

The clarity of hair gels were measured by using Hach Laboratory Turbidimeter (Model 2100N). The instrument is designed for measurement of turbidity from 0 to 4000 NTU (Nephelometric Turbidity Units) with automatic range selection and decimal point placement. Low turbidity reading represents high clarity. The turbidity values of clear to translucent hair gels containing xanthan gum and heat-treated xanthan gum are listed in Table 5. The turbidity values of three clear commercial hair gels are also listed as a reference.

TABLE 5

| Hair Styling Gel Compositions | Turbidity (NTU) |
|---|---|
| 4% Acrylates Copolymer + 1% untreated xanthan gum (Formula 19) | 18.5 |
| 4% Acrylates Copolymer + 1% heat-treated xanthan gum (fluid bed @ 220° F. for 120 minutes) | 24.2 |
| 4% Acrylates Copolymer + 1% heat-treated xanthan gum (fluid bed @ 220° F. for 150 minutes) | 25.2 |
| 4% Acrylates Copolymer + 1% heat-treated xanthan gum (fluid bed @ 228° F. for 60 minutes) | 23.7 |
| 4% Acrylates Copolymer + 1% heat-treated xanthan gum (fluid bed @ 228° F. for 90 minutes) | 24.5 |

TABLE 5-continued

| Hair Styling Gel Compositions | Turbidity (NTU) |
|---|---|
| 4% Acrylates Copolymer + 1% heat-treated xanthan gum (fluid bed @ 235° F. for 60 minutes) | 25.3 |
| 1% heat-treated xanthan gum (fluid bed @ 235° F. for 60 minutes) | 24.2 |
| Commercial hair gel (containing PVP, PVP/VA, carbomer, and other additives) | 15.0 |
| Commercial hair gel (containing PVP, carbomer, and other additives) | 14.0 |
| Commercial hair gel (containing PVP, carbomer, and other additives) | 10.9 |
| Deionized water | 0.04 |

Example 7

Hair Spray Gel with Xanthan Gum

| Ingredients | % w/w | % w/w |
|---|---|---|
| Part A | | |
| Acrylates Copolymer[1] (50%) | 8.0 | 8.0. |
| D.I. Water | 40.0 | 40.0 |
| Aminomethyl Propanol[2] | 0.56 | 0.56 |
| Part B | | |
| Xanthan gum[3] | 0.5 | — |
| Heat-treated Xanthan gum[4] | — | 0.3 |
| Deionized Water | q.s. | q.s. |
| Preservative | q.s. | q.s. |
| Part C | | |
| Keratin Protein | 0.2 | 0.2 |
| Propylene Glycol | 2.0 | 2.0 |
| Polysorbate 20[4] | 0.5 | 0.5 |
| Fragrance | 0.1 | 0.1 |

[1]Balance 0/55 (National Starch and Chemical Co.)
[2]AMP-95 (Angus)
[3]Keltrol T (Kelco)
[4]Heat-treated Keltrol T (Fluid bed reactor at 235° F. for 60 minutes)
[5]Tween 20 (ICI Surfactants)

Example 8

Hair Mousse with Xanthan Gum

A. Surfactant-free Hair Mousse with Xanthan Gum

| Ingredients | % w/w |
|---|---|
| Acrylates Copolymer[1] (50%) | 8.0 |
| D.I. Water | 40.0 |
| Aminomethyl Propanol[2] | 0.56 |
| Xanthan gum[3] | 0.4 |
| Deionized Water | q.s. |
| Preservative | q.s. |
| Part C | |
| Isobutane/Propane[4] | 6.0 |
| | 100 |

[1]Balance 0/55 (National Starch and Chemical Co.)
[2]AMP-95 (Angus)
[3]Keltrol T (Kelco)
[4]Propellant A-46

| B. 6% VOC Mousse with Heat-Treated Xanthan Gum | | | |
|---|---|---|---|
| Ingredients | % w/w | % w/w | % w/w |
| Heat-treated Xanthan gum[1] | 0.6 | 0.6 | 0.6 |
| Propylene Glycol | 1.0 | 1.0 | 1.0 |
| Brij 30[2] | 0.4 | 0.2 | — |
| DC 193[3] | 0.2 | 0.2 | 0.2 |
| Dowicil 200[4] | 0.2 | 0.2 | 0.2 |
| Deionized Water | 91.6 | 91.8 | 92.0 |
| Propellant A-46[5] | 6.0 | 6.0 | 6.0 |
| | 100 | 100 | 100 |

[1]Heat-treated ADM xanthan gum (Fluid bed reactor at 220° F. for 180 minutes)
[2]Laureth-4 (Uniqema)
[3]Dimethicone Copolyol (Dow Corning)
[4]Quaternium-15 (Dow Chemical Co.)
[5]Isobutane/Propane Xanthan gum is suited for use in any type of styling mousses, including 6% VOC mousses and surfactant-free mousses. In addition to providing hold to the mousses, Xanthan contributes to the conditioning and non-tacky feel.

Example 9

Styling Mousse

| Ingredients | % w/w |
|---|---|
| Sodium Polystyrene Sulfonate[1] | 10.0 |
| Polysorbate 20[2] | 0.4 |
| Nonoxynol-15[3] | 0.4 |
| Oleth-10[4] | 0.4 |
| Xanthan gum[5] | 0.5 |
| Deionized Water | 68.3 |
| SD Alcohol 40 | 10.0 |
| Isobutane | 10.0 |
| | 100 |

[1]Flexan 130 (National Starch and Chemical Co.)
[2]Tween 20 (Uniqema)
[3]Tergitol NP-15 (Uniqema)
[4]Brij 97 (Uniqema)
[5]Keltrol T (Kelko)

Example 10

Aerosol Hair Spray

| Ingredients | % w/w |
|---|---|
| Octylacrylamide/Acrylates/Butylaminoethyl Methacrylate Copolymer[1] | 8.0 |
| Aminomethyl Propanol[2] | 1.38 |
| Xanthan gum[3] | 0.3 |
| Deionized Water | 45.32 |
| SD Alcohol 40 | 20.0 |
| Fragrance | q.s. |
| Preservative | q.s. |
| Dimethyl Ether | 25.0 |
| | 100 |

[1]Balance 47 (National Starch and Chemical Co.)
[2]AMP (Angus)
[3]Keltrol T (Kelko)

Example 11

Hair Styling and Conditioning Cream

| Ingredients | % w/w |
|---|---|
| Part A | |
| Deionized Water | q.s. |
| Heat-treated xanthan gum[1] | 0.7 |
| Quaternium-4[2] | 0.15 |
| Part B | |
| Glyceryl Stearate[3] | 2.0 |
| Jojoba oil | 2.0 |
| Part C | |
| Fragrance | q.s. |
| Preservative | q.s. |
| | 100 |

[1]Heat-treated Keltrol T (Fluid bed reactor at 235° F. for 60 minutes)
[2]Celquat H-100 (National Starch and Chemical Co.)
[3]Cerasynt SD (ISP)

Example 12

Varying Viscosity and Crossover Strain of Heat treated Xanthan Gums

Several of the heat treated xanthan gums used in the examples above were tested to determine their viscosity and crossover strain in a 1% aqueous solution. The xanthan gums were commercially available and the results are shown below.

| Sample | Viscosity* (cps) | Crossover Strain (%) |
|---|---|---|
| ADM xanthan treated at 220° F. for 180 minutes | 35600 | 25 |
| Keltrol T treated at 235° F. for 60 minutes | 13100 | 82 |
| Keltrol T treated at 220° F. for 240 minutes | 18200 | 35 |

*viscosity is measured using a Brookfield DV-I viscometer with Sprindle #6 @ 10 rpm

We claim:

1. A cosmetic composition comprising a fixative effective amount of heat treated xanthan gum for fixing hair, and a second fixative polymer comprising polyvinylpyrrolidone or a copolymer of polyvinylpyrrolidone:
   wherein the xanthan gum has been heat treated at a temperature of about 60° C. or more for about 30 minutes or more to a moisture content of about 8% or less,
   wherein the heat-treated xanthan gum has a viscosity of about 4000 cps or greater and a crossover strain of about 100 or less in a 1% aqueous solution,
   wherein the cosmetic composition is a hair fixative cosmetic composition, and
   wherein the fixative cosmetic composition provides an improved high humidity curl retention of hair over fixative cosmetic composition without the heat treated xanthan gum.

2. The composition of claim 1, wherein the temperature is at least 100° C.

3. The composition of claim 2, wherein the temperature is at least 105° C.

4. The composition of claim 1, wherein the moisture content is about 1% or less.

5. The composition of claim 1, wherein the heat treatment is for about one hour or more.

6. The composition of claim 5, wherein the heat treatment is for about 2.5 hours or more.

7. The composition of claim 1, wherein the heat treatment is at a temperature of about 105° C. or more for about 2.5 hours or more to a moisture content of about 1% or less.

8. The composition of claim 1, wherein the composition is selected from the group consisting of a spray, a mousse, a hair lotion, a cream, a pomade, and a gel.

9. The composition of claim 8, wherein the composition is a gel.

10. The composition of claim 1 wherein the heat treated xanthan gum has a viscosity of about 8000 cps or more and a turbidity of no more than about 100 NTU (Nephelometric Turbidity Units).

11. The composition of claim 1 further comprising a fixative polymer selected from the group consisting of acrylates copolymer, octylacrylamide/acrylates/butylaminoethyl methacrylate copolymer, acrylates/octylacrylamide copolymer, VA/crotonates/vinyl Neodeanoate copolymer, poly(N-vinyl acetamide), poly(N-vinyl formamide), polyurethane, corn starch modified, sodium polystyrene sulfonate, polyquaternium-4, polyquaternium-10 and polyurethane/acrylates copolymer.

12. A method of preparing the composition of claim 1, comprising dispersing the xanthan gum in water; and mixing in other hair cosmetic components.

13. A method of providing fixative properties to hair comprising applying the composition of claim 1 to the hair.

14. A method of providing curl retention of hair under high humidity conditions comprising applying the composition of claim 1 to hair.

15. The composition of claim 1, wherein the composition is a surfactant-free hair mousse.

16. A cosmetic composition comprising:
a fixative, wherein the fixative is essentially heat treated xanthan gum wherein the heat treated xanthan gum has been heat treated to a moisture content of about 8% or less, wherein the heat-treated xanthan gum has a viscosity of about 4000 cps or greater and a crossover strain of about 100 or less in a 1% aqueous solution; and
a second fixative polymer comprising polyvinylpyrrolidone or a copolymer of polyvinylpyrrolidone;
wherein the cosmetic composition is a hair fixative cosmetic composition and provides an improved high humidity curl retention.

17. The composition of claim 16, wherein the composition is selected from the group consisting of a spray, a mousse, a hair lotion, a cream, a pomade, and a gel.

18. The composition of claim 17, wherein the composition is a gel.

19. The composition of claim 16 characterized by a viscosity of about 8000 cps or more, a high humidity curl retention of about 80% or more and a turbidity of no more than about 100 NTU (Nephelometric Turbidity Units).

20. The composition of claim 16, wherein the composition is a surfactant-free hair mousse.

21. The composition of claim 1 wherein the second fixative polymer is selected from the group consisting of PVP/dimethylaminoethylmethacrylate copolymer, PVP/vinylcaprolactam/DMAPA acrylates copolymer, Vinyl caprolactam/PVP/dimethylaminoethyl methacrylates copolymer, polyvinylpyrrolidone, PVP/vinyl acetate copolymer, PVP/acrylates copolymer, vinylcaprolactam/PVP/dimethylaminoethyl methacrylate.

22. The composition of claim 16 wherein the second fixative polymer is selected from the group consisting of PVP/dimethylaminoethylmethacrylate copolymer, PVP/vinylcaprolactam/DMAPA acrylates copolymer, Vinyl caprolactam/PVP/dimethylaminoethyl methacrylates copolymer, polyvinylpyrrolidone, PVP/vinyl acetate copolymer, PVP/acrylates copolymer, vinylcaprolactam/PVP/dimethylaminoethyl methacrylate.

23. The composition of claim 1 wherein the second fixative polymer is polyvinylpyrrolidone.

24. The composition of claim 16 wherein the second fixative polymer is polyvinylpyrrolidone.

* * * * *

UNITED STATES PATENT AND TRADEMARK OFFICE
CERTIFICATE OF CORRECTION

| | | |
|---|---|---|
| PATENT NO. | : 9,072,683 B2 | Page 1 of 1 |
| APPLICATION NO. | : 10/198469 | |
| DATED | : July 7, 2015 | |
| INVENTOR(S) | : Cao et al. | |

It is certified that error appears in the above-identified patent and that said Letters Patent is hereby corrected as shown below:

Specification
Column 7, line 11, "$^1$Balance 47" -- should read -- $^2$Balance 47 --.

Signed and Sealed this
Twenty-ninth Day of March, 2016

Michelle K. Lee
*Director of the United States Patent and Trademark Office*